(12) United States Patent
Spindell et al.

(10) Patent No.: US 11,516,435 B1
(45) Date of Patent: Nov. 29, 2022

(54) SYSTEM AND METHOD OF CONTACTING DEVICES AND CREATING A COMMUNICATION SESSION

(71) Applicant: Get Heal, Inc., Los Angeles, CA (US)

(72) Inventors: Henry Spindell, San Diego, CA (US); Anthony Persaud, San Diego, CA (US); Andrew Flores, San Diego, CA (US); Salvatore Nuziale, Playa Vista, CA (US); Avery Ryder, San Diego, CA (US); Jaewook Chun, San Diego, CA (US)

(73) Assignee: Get Heal, Inc., Los Angeles, CA (US)

( * ) Notice: Subject to any disclaimer, the term of this patent is extended or adjusted under 35 U.S.C. 154(b) by 0 days.

(21) Appl. No.: 17/363,932

(22) Filed: Jun. 30, 2021

(51) Int. Cl.
  *H04N 7/15* (2006.01)
  *G16H 80/00* (2018.01)
  *G16H 40/67* (2018.01)
  *H04N 7/14* (2006.01)

(52) U.S. Cl.
  CPC .............. *H04N 7/155* (2013.01); *G16H 40/67* (2018.01); *G16H 80/00* (2018.01); *H04N 7/147* (2013.01)

(58) Field of Classification Search
  CPC ........... H04N 7/15; H04N 7/14; G16H 40/67; G16H 80/00; G16H 10/00
  USPC ............................................. 348/14.01–14.16
  See application file for complete search history.

(56) References Cited

U.S. PATENT DOCUMENTS

| | | | |
|---|---|---|---|
| 2005/0264649 A1* | 12/2005 | Chang | F16M 13/00 348/E7.079 |
| 2016/0241606 A1* | 8/2016 | Calamera | H04L 65/1069 |
| 2017/0193457 A1* | 7/2017 | Shukla | H04L 65/403 |
| 2018/0337927 A1* | 11/2018 | Carnahan | H04L 63/0876 |
| 2019/0037175 A1* | 1/2019 | Vitale | H04M 3/563 |
| 2019/0182223 A1* | 6/2019 | Wang | H04L 63/0892 |
| 2020/0020437 A1* | 1/2020 | Sanjay-Gopal | G06F 9/4451 |
| 2021/0084040 A1* | 3/2021 | Sakowicz | H04L 63/1425 |

\* cited by examiner

*Primary Examiner* — Melur Ramakrishnaiah
(74) *Attorney, Agent, or Firm* — Burns & Levinson LLP; Daniel McGrath, Esq.

(57) ABSTRACT

A system and method of video communication between participants operating one of a plurality of devices. The system generates a list of registered users each associated with at least one device and generates a fingerprint for each device. A provider requests a communication session, from the system, with at least one user identified by the provider. The system then generates a participant list of users for the communication session and an access code authorizing access to the communication session and sends the access code to the provider. The provider enters the access code and the system determines a notification type for each device associated with users on the participant list based on the fingerprint for said device, provides a notification to each device associated with users on the participant list, and sends a notification and access code. The user device then joins the communication session with the access code.

13 Claims, 4 Drawing Sheets

SYSTEM AND METHOD OF CONTACTING DEVICES AND CREATING A COMMUNICATION SESSION

FIELD OF THE TECHNOLOGY

The subject disclosure relates to secure data exchange between devices, and more particularly, systems and methods for reaching out to particular devices for participation in a communication session.

BACKGROUND OF THE TECHNOLOGY

Video calls are becoming an increasingly popular way of communicating. While various systems exist for carrying out video calls between devices, different business and social environments present different needs which are unmet by existing video call technology. For example, when schedules are unpredictable, video calls sometimes must be made on-demand (i.e. at a given moment, rather than at a pre-scheduled time). This presents issues for systems which require scheduling ahead of time. Further, it can be difficult to identify and contact all necessary participants for a given meeting. Oftentimes, different participants will be using different types of devices, making one set method of notifying all participants of the meeting ineffective (e.g. if a notification goes out only by e-mail or text to all participants). Additionally, an individual user may have many different devices, but may not have each device with them at all times. Therefore if the wrong device is notified of the meeting, that individual may never be aware that the meeting is taking place.

Telemedicine is one example of an environment where existing video call technology falls short. In addition to the challenges presented above, patients participating in a telemedicine call often need the participation of other individuals in their telemedicine visit, such as a caregiver or guardian of the patient, or a third-party interpreter. While those related individuals must be contacted and added to the video call, existing video call system are limited in their ability to do so. Finally, access to the video call must be carried out in a secure manner, to ensure unauthorized users cannot join the call and no sensitive information about the participants is released outside the video call.

SUMMARY OF THE TECHNOLOGY

In at least one aspect, the subject technology relates to a method of video communication between participants operating one of a plurality of devices, the participants including at least one user and a provider and the devices including at least one user device running a user application and a provider device running a provider application. The method includes: a) generating, by the system, a list of registered users each associated with at least one of the user devices; b) generating, by the system, a fingerprint for each of the devices associated with a registered user, each fingerprint being a unique digital identifier for a corresponding device; c) requesting, by a provider and from the system, a communication session with at least one user identified by the provider; d) in response to the request by the provider, generating, by the system, a participant list of users for the communication session and an access code authorizing access to the communication session, wherein the system sends the access code to the provider; e) determining, by the system, all user devices associated with users identified by the provider; f) entering, by the provider, the access code in the provider application of the provider device to initiate the communication session; g) in response to the provider entering the access code, determining, by the system, a notification type for each device associated with users on the participant list based on the fingerprint for said device, and providing a notification to each device associated with users on the participant list based on the notification type determined for said device, wherein each notification includes a payload containing an access code authorizing access to the communication session; and h) when at least one user device answers the notification and receives the access code, using the access code to join the communication session, by said user device.

In some embodiments, the subject technology includes, during step a), registering devices, by the system, by one or more of the following ways: providing a URL associated with the system, to the device, the URL then being accessed by the device to register the device; or by running the user application. In some cases, during step d), the participant list includes users from the list of registered users, and at least one unregistered user.

In some embodiments, at least one user on the participant list is a patient and the system selects at least one additional user to add to the participant list based on the patient. In some cases, the at least one additional user is a translator, selected by the system based on a native language of the patient. In some cases, the at least one additional user is selected based on a relationship to the patient, including at least one of the following: a relative; a guardian; or a caregiver.

In some embodiments, the at least one user on the participant list is a patient and the communication session is a telemedicine session including video communication between participants. In some cases, each fingerprint is an algorithm built from device properties for the corresponding device, account properties for an account of an associated user, and session properties for the communication session. In some embodiments, during step g): when a user is associated with multiple devices, the user receives notifications simultaneously on all associated devices; and upon answering a notification on one device and joining the communication session by a user, all notifications to other devices associated with said user are terminated.

In some embodiments, during step h), upon answering a notification on a device, the device automatically joins the communication session using the access code. In some cases, prior to joining the communication session, all participants redeem their access code for an access token based on the access code, the access token authorizing access to a video room for the communication session. In some cases, each participant is associated with a particular access code, and redeeming an access code with a device prevents subsequent redemption of the same access code by a different device. In some embodiments, the notification types include at least the following: a push notification; an email notification; and a text notification.

BRIEF DESCRIPTION OF THE DRAWINGS

So that those having ordinary skill in the art to which the disclosed system pertains will more readily understand how to make and use the same, reference may be had to the following drawings.

DETAILED DESCRIPTION

The subject technology overcomes many of the prior art problems associated with secure data exchange. In brief summary, the subject technology provides a system and method for reliably contacting users via their devices and carrying out a video call. While the subject technology can be implemented in various environments, the subject technology has been found to be particularly advantageous when used in a telemedicine environment, as the technology can be utilized for a HIPAA compliant video conference between a patient and provider. The advantages, and other features of the systems and methods disclosed herein, will become more readily apparent to those having ordinary skill in the art from the following detailed description of certain preferred embodiments taken in conjunction with the drawings which set forth representative embodiments of the subject technology.

Figure 1:
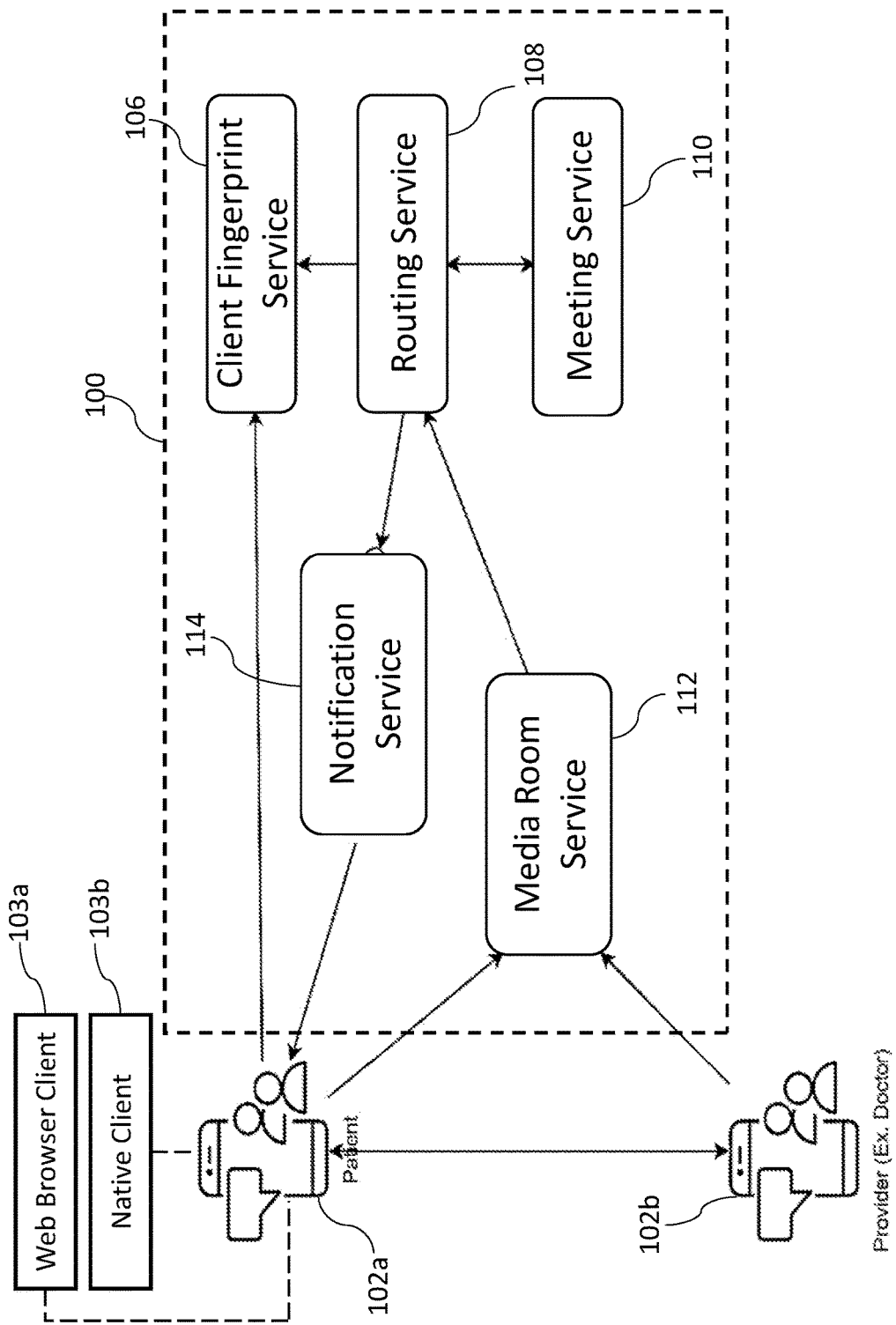
FIG. 1 is a block diagram of a system for contacting devices and creating a communication session in accordance with the subject technology.

Referring now to FIG. 1, a block diagram of a system 100 for contacting devices 102a, 102b (generally 102) and creating a communication session in accordance with the subject technology is shown. The system 100 includes a number of modules which carry out various tasks, as will be described in more detail below. The system 100 ultimately facilitates communication between the users of the various devices 102, who are participants in the communication session. The devices 102 are generally systems which allow for video data transfer for electronic communication, such as a smartphone or laptop, and which are operated by various individuals who will participate in a communication session. For the system 100 to work, the devices 102 must be capable of receiving an on-demand meeting invite. Thus, devices 102 will normally include an internet connection and access to a web browser 103a or installed native application 103b for the system. While the process described herein can be carried out in in a number of different environments, an exemplary application within a telemedicine environment is provided below. It should be understood that the process could also be carried out in other environments where a video call between users operating devices 102 is desired.

In a telemedicine application, at least one provider (e.g. doctor, physician assistant, nurse, etc.) will operate a provider device 102b during the communication session, the provider device 102b connecting with one or more user devices 102a operated by one or more patients to carry out a telemedicine video call. The system 100 can also allow additional user devices 102a operated by other pertinent individuals, such as a caregiver, guardian, or relative of the patient, or a translator if needed (selected based on a native language of the patient), to participate in the telemedicine video call. The system 100 can store data related to the devices 102 and the individuals who operate those devices 102, and facilitate an on-demand peer to peer video connection between devices 102 for a telemedicine call. As doctors and other healthcare providers tend to have fluid and unpredictable schedules, this capability eliminates the necessity of patients actively waiting for a scheduled appointment to begin. This is accomplished, in part, by fingerprinting devices 102 with a hash algorithm, with the fingerprints being processed later to determine the correct channels through which to reach said devices 102.

Through the system 100, healthcare providers have a list of patients whom they can reach at any time for a video call. In some cases, all devices 102 on the system 100 can have an application associated with the system 100 installed, and running the application on the device 102 can register the device 102 with the system 100. Registration of a device 102 will store information about the device 102 within the system 100. Alternatively, devices 102 can be initially registered with the system in a number of ways, such as by visiting a URL associated with the system 100 which records data about the device 102 when accessed. When the device 102 is registered, further information is stored about the patient or provider corresponding to the registered device 102 so that the patient is also registered with the system 100. This can be accomplished by providing an option for a user, such as a patient, to create a user profile by entering their name, date of birth, and other relevant information about themselves through the application. This list of registered devices and users can be relied on to provide a list of patients for the provider to select from for a telemedicine call. Once a user device 102a is registered, it can be called by a provider, using a provider device 102b, through the system 100. In some cases, the system 100 can also allow a provider to video call unregistered devices 102, for example, when unregistered devices 102 associated with individuals such as a caregiver, guardian, or third-party interpreter services are appropriate for a given telemedicine visit. In the case of an unregistered device 102 the system 100 uses a link delivery vehicle, such as an email address or phone number associated with the unregistered device 102.

When a user device 102a launches the application associated with the system 100, or goes to a predetermined URL, a client fingerprint service 106 registers the device 102a and generates a fingerprint for that particular user device 102a. The fingerprint can include device, account, and session properties. In general, device properties relate to an attribute or identifier pertaining to the specific hardware (or device-level software) on which the application or browser is running. Device properties may be related to model, manufacturer, production serial numbers, operating system, AV permissions, etc. Account properties generally relate to an attribute of the user's registered profile within the system 100, such as notification preferences. Session properties can refer to user's activity within the application in the active timeframe, such as time and location of last login, the user's most recent action. Thus, among other things, the properties include the time of activity, platform (operating system), app installation status, login status, audio/video permissions on the device, push notifications, and user communication preferences. All of this data is hashed and sent to a notification service 114 (discussed in more detail below) to be associated with a patient and stored for later use. When the provider wants to start the telemedicine visit with the user, the provider can do so through a dedicated application on their own device (i.e. provider device 102b). Through the application on the provider device 102b, the provider can select a recipient who will receive telemedicine services. This can be done by selecting a particular individual from the list of people with registered user devices 102a. Alternatively, if the provider has an e-mail address or phone number for an individual who has not registered a device 102b, the provider can select the recipient by e-mail or phone number. There are additional circumstances in which users may become disassociated with a device. When a user explicitly logs out of their account, the device they used for the logout action is sometimes considered inactive and removed from the registry. However, a user may also uninstall an application or cease using it for other reasons that are difficult to automatically detect. To ensure all device registrations are up to date and valid for a user, fingerprints can be refreshed on each session and a device can be disassociated from the user if not refreshed over a specified time period (e.g. two weeks).

The provider than initiates a video call. There are two ways a provider may initiate an on-demand call to a patient from the dedicated provider application. The first is by choosing from a list of registered patients. When the provider chooses a patient, the routing service requests that the media room service 112 create a new ad hoc meeting beginning immediately (as opposed to appointments scheduled far ahead of time). This request, and consequently the meeting participant object, contains information about the patient so that the system can later contextualize events that occur inside the video call.

Therefore the provider application then sends a request to a routing service 108 to begin a telemedicine call immediately with the chosen recipient. The routing service 108 requests a meeting service 110 to provision a meeting and the meeting service 110 generates the meeting object including metadata describing the provider and patient entities. The provider and patient entities described within the meeting object can include their participant identifiers, access PINs, and other metadata such as display name, role, or avatar URLs (derived from provider/patient profiles registered in system 100). If the recipient is unregistered, the routing service 108 stores association data in a temporary key value store. Once the meeting is created, a secure access code specific to the host (provider) is generated and returned to the provider application. The provider enters the meeting using the access code, triggering the asynchronous invite process to the patient receiving the call. The routing service 108 then takes the meeting object generated by the meeting service 110 and returns the provider's designated secure access code to the provider, via the provider device 102*b* and using provider application.

The provider application then sends the access code to the meeting service 110. The meeting service 110 then validates the access code and asks a media room service 112 to generate a video room access token. The access token is stateless and contains a unique meeting identifier with information particular to the communication session and the devices 102 authorized to participate. The meeting service 110 then returns the access token to the provider application of the provider device 102*b*. The provider application redeems the access token with the media room service 112 which provides access to, and begins, the video call. The media room service 112 then sends an event payload, notifying the meeting service 110 that a specific participant has entered the video call. The meeting service 110 uses data that is previously registered and stored with the system 100 to determine the meeting and participant relevant to the event payload. The meeting service 110 forwards the event payload, with added contextual metadata (from the metadata generated by the meeting service 110, as described above), to the routing service 108. The routing service 108 then determines the meeting described by the event payload, and its participant identities, by using metadata from the meeting service 110 and additional data about the participants. In the case where patients were previously registered with the system 100, the routing service 108 additionally relies on the registered patient information. In the event the patient has not been registered, the routing service 108 can rely on information from a key value store (discussed in more detail below).

Upon interpreting that the provider (i.e. the host) has joined the meeting, the routing service 108 begins determining an optimal way to deliver an invitation to join the meeting to a patient. The routing service 108 queries the client fingerprinting service 106 for information about devices 102*a* belonging to patient, including fingerprints for those devices 102*a*. The routing service 108 then uses the fingerprint to algorithmically choose the optimal communication type and vendor for that patient's device 102*a*. The optimal communication type and vendor include a designated route for receiving a secure access code and/or link for accessing the video call. Therefore the routing service 108 can then request a notification service 114 deliver the patient's designated secure access code/link via the designated route. Since the native call interface is considered the best user experience on mobile, the first option is checking if the recipient user has registered for notifications on a mobile device. The routing service queries the notification service with a user ID, which in turn queries its device registry (client fingerprint service 106) to review registered device fingerprints for that user and return any that are valid for accepting push video calls. Certain fingerprint properties may make a device ineligible for telemedicine, such as declined audio/video permissions, being logged out, or not having been seen/refreshed in a long time (expiration). If there are eligible devices available for the user, the routing service 108 makes another POST to the notification service 114, this time with a data payload containing a secure individualized access link, generated by the video service, for the patient. A push notification is sent to each eligible device simultaneously.

Notably, one individual may have multiple devices 102 registered with the system, and the system 100 can determine, for each registered device 102, the correct channel to send a notification through. The notification service 114 delivers the access code or link to the patient via the vendor specified channel. The user device 102*a* then receives the invitation and can perform some checks, such as whether the device is prepared to join a call (e.g. has camera and microphone access), based on its fingerprint, before exchanging the access code for an access token to the video room to join the video conference, as previously described. Once the access token has been obtained, the user device 102*a*, and therefore the patient, may join the video call. When an access code for a patient is sent to multiple devices 102*a*, joining the video call with one device 102*a* of that patient will result in no further notifications being sent to other devices 102*a* for that patient.

In this way, the system 100 facilitates the delivery of a secure, individualized access link to patients that will allow them to join a telemedicine call. The method of outreach to each device 102 for delivering that link is determined by the routing service 108. The routing service 108 listens to events sent from the media room service 112, such as who has joined the call and when, and resolves these event payloads to existing resources in the system 100. When the event from the media room service 112 has been resolved to determine the identity of the meeting's participants, the routing service 108 determines the next action and how to notify the relevant participants of that action. A patient will receive a call (e.g. a video call) when the provider successfully joins the call they have initiated. Push notifications serve as a smooth lead-in to the native call experience on devices 102, so this invitation method is prioritized where possible.

Devices 102 that are push-capable register themselves as such in a database. In the event a user has not registered any devices, they can still be reached via email and SMS (text). Launching the link provided by the system 100 on a mobile device opens the telemedicine call in a native application if it is installed (iOS or Android). If the application is not installed, or the device 102 is a web browser, the telemedicine call is joined on the web platform for the media room service 114. Providers and patients do not need to connect from the same device type.

Figure 2A:
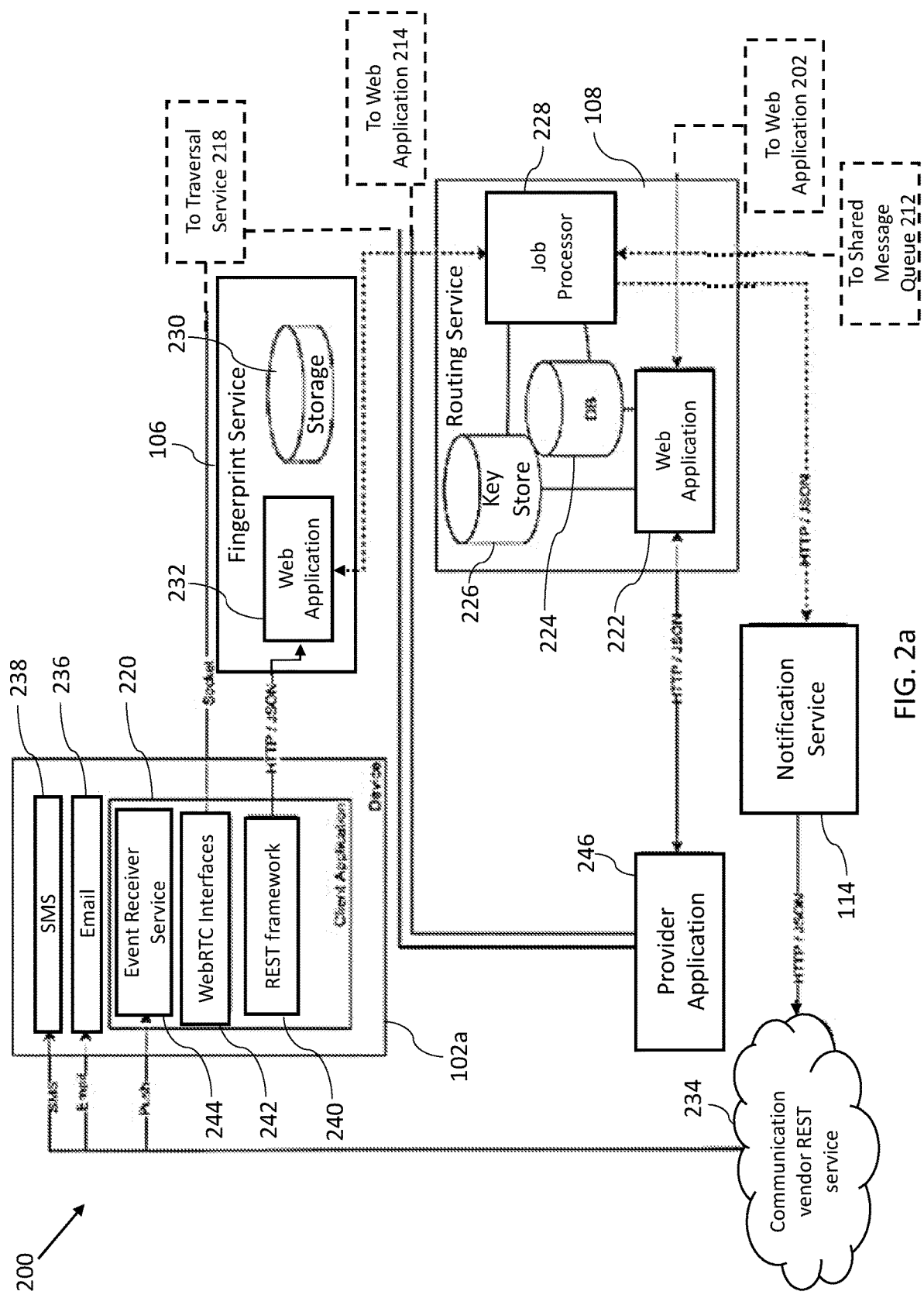
FIGS. 2a-2b are a block diagram of exemplary system architecture for the system for a system in accordance with the subject technology.
Figure 2B:
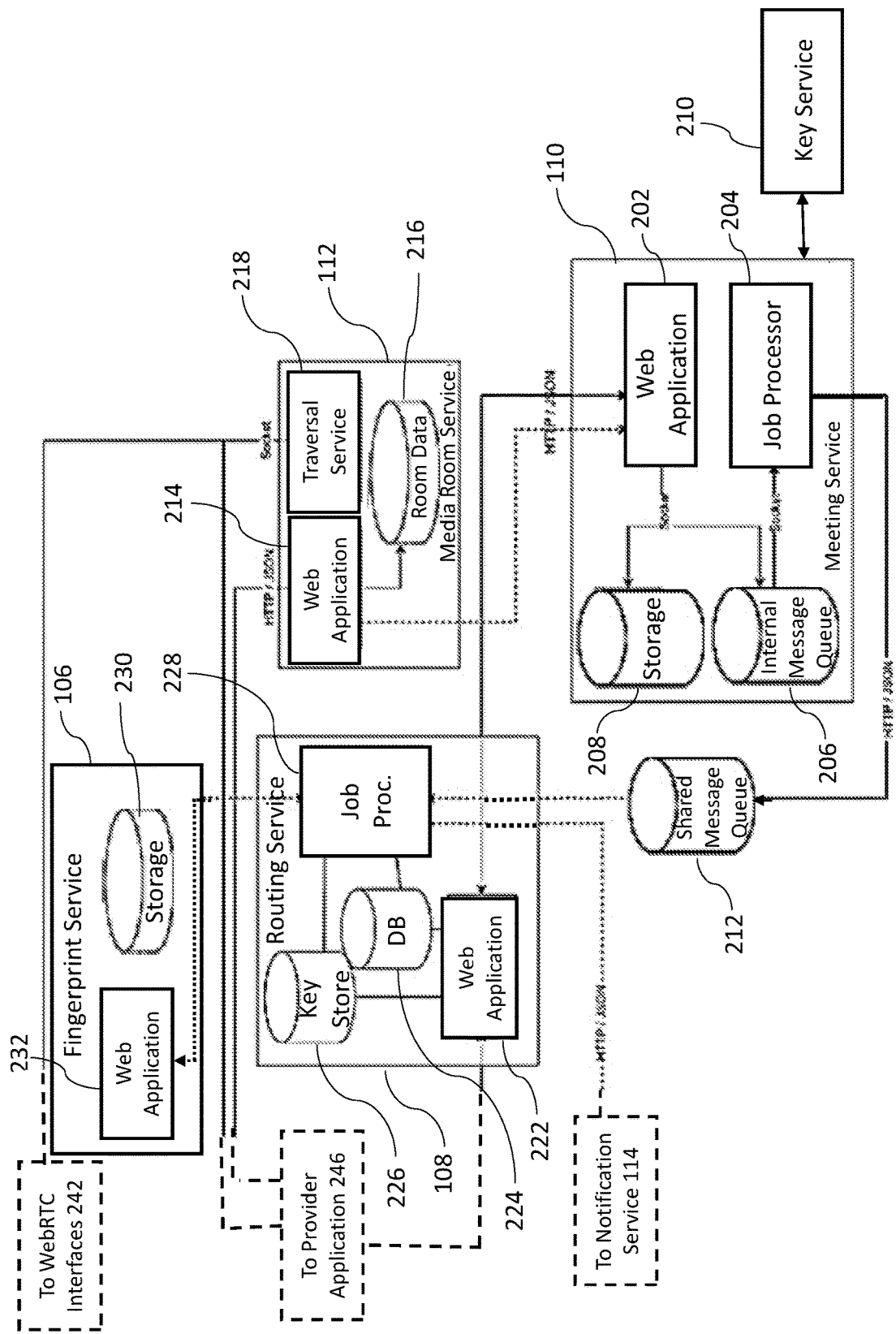

Referring now to FIGS. 2a-2b, a block diagram 200 of exemplary system architecture for the system 100 is shown. The block diagram 200 is divided into two separate figures (FIG. 2a and FIG. 2b) for clarity of illustration, but it should be understood that each figure represents a portion of the same block diagram 200 for the same system 100. While other systems and/or components may also be included, the components shown in the block diagram 200 are representative of one exemplary configuration of certain components for the system 100. Routine and conventional components may also be included as part of the system 100, as would be understood by one of skill and the art, but are not specifically shown and described herein.

The system 100 includes a key service 210 which generates secure-random Universally Unique Identifiers (UUIDs) including identifiers for a particular meeting (i.e. a communication session), and for a particular participant. Using the set of identifiers listed, the key service 210 can also generate a specific short-code format for authentication, and can encode and decode short-code format links. Further, the key service 210 can cryptographically sign, using a secret only known to the key service 210, and create access token payloads.

The system 100 also includes a meeting service 110 (FIG. 2b) which is composed of an API REST web application 202, an asynchronous job processor 204, an internal message queue 206, and database storage engine 208. The responsibility of the meeting service 110 is to interact with API requests (clients and other servers), process the payload and perform business logic, including: (1) Creating telemedicine meetings within a specified Time-Window; (2) Interacting with the Key Service 210 to generate and decode secure-random information; (3) Enqueue at scale tasks such as notifications for further processing; (4) Listen for incoming event triggers from the media room service 112, including the event when a participant connects/disconnects to a room for a video call.

As part of the meeting service 110, the API REST web application 202 (or web application 202) utilizes the standard HTTPS web protocol with a JSON payload to receive incoming API requests from clients through the internet (e.g. through cellular, WiFi, or the like). It exposes a standard REST API to clients. Internally the web application 202 communicates with the database storage 208 and message queue 206 through a socket connection. In some implementations, the web application 202 can be a RACK-based web application (i.e. a standard web application on Ruby containing middleware software). The system 100 also includes storage 208, which is a database used to store all meeting information, including all details of meeting objects for various meetings. In some implementations, the storage 208 can be a NoSQL database (non-structured, such as MongoDB) in order to store all the details of a meeting object without requiring relations to any other data in the system 100 (one large structured document).

The internal message queue 206, or message queue 206, is used to communicate between the web application 202 and the job processor 204. The message queue 206 is a standard message queue system where messages that can be interpreted as "tasks or jobs" can be enqueued and later processed by the job processor 204. This allows the web application 202 to be highly performant and delay any tasks that can be done at a later time, and also to properly throttle a large volume of tasks. This can be implemented with a standard key-value store such as REDIS. One advantage of using the message queue 206, rather than a direct connection between the web application 202 and job processor 204, is to allow for persistent storage of these messages in the case the job processor 204 is down or unavailable. If the job processor 204 comes back online from a fault, the job processor 204 can then retrieve the pending messages from the message queue 206.

The job processor 204 is a long running application that is triggered when messages are added to the message queue 206. Every message in the message queue 206 is interpreted as a task that can be done by the job processor 204. The job processor 204 is in charge of notifying the routing service 108 depending on the actions and events that are triggered by the web application 202. This can include getting meeting, participant, and key information that needs to be sent to target devices to allow those participants to join the meeting. Separating the job processor 204 from the web application 202 allows large volumes of tasks to be processed asynchronously given that any web application would block if they had to perform the task themselves. This is due to web applications being limited to the number of active client connections at a given time and when a client connects to the web application 202, the connection is maintained until the entire work task is completed. If the web application 202 had to perform the entire task (e.g. including talking to several systems, dealing with timeouts, unable to retry work, interacting with routing service 108), it could become a bottleneck as future clients trying to connect to the web application 202 have to either hold or continue retrying until the web application 202 is able to service their request. This also makes the system 100 fault-tolerant, because in the event that the job processor 204 goes down in the interim, the messages in the message queue 206 are persisted until the job processor 204 is back online, assuring notifications go out to clients as needed. The job processor 204 communicates with the notification service 114 through another global shared message queue (212), which can be a standard Amazon Web Services Simple Queuing Service (SQS), which the notification service 114 listens to for events.

The media room service 112 is built with three components, including an authenticator REST web application 214 (or authenticator web application 214), a room database 216 and a network traversal service 218. The authenticator web application 214 is a service that receives an access token that has been signed by the meeting service 110. The access token is stateless and contains signed metadata, so there is no need to communicate with the meeting service 110 to verify its authenticity. Upon validation of the signed token, the authenticator web application 214 uses information in the token, which contains a unique and secure random meeting identifier, to create an entry in the room database 216 which stores "meeting room" data for the meeting.

A user application 220 (FIG. 2a) on a user device 102a then provides a publicly available IP (Internet Protocol) address and socket information that it will use to allow incoming connections for the peer-to-peer network. The authenticator web application 214 then stores user information and associates this information to the meeting in the room database 216.

The room database 216 is implemented as a key-value store (e.g. a standard REDIS database), where the key value is the meeting identifier, which doubles as the room identifier, and a list of participant identifiers and IP address pairs that are connected to the room. The IP addresses are provided by the client applications 220 when they authenticate to the authenticator service.

The network traversal service 218 can be a standard STUN/TURN protocol enabled service to support signaling and network traversal when creating peer-to-peer networks. This supports WebRTC (audio/video) over the internet when there are many firewalls and routers that may block clients from exposing public ports. All WebRTC clients, including the applications discussed herein, support using a STUN/TURN service.

The job of the routing service 108 is to receive events from the shared message queue interface 212 with the fingerprint service 106 to best provide direction to the notification service 114 and reach remote users. Channels by which users can be reached include push notifications, VoIP, SMS, and email. The routing service 108 includes an API REST web application 222 (or web application 222), a database storage 224, a key-value store 226, and a job processor 228.

The web application 222 utilizes the standard HTTPS web protocol with a JSON payload to receive incoming API requests from clients (e.g. devices) through the internet (e.g. through cellular, WiFi, or the like). It exposes a standard REST API to clients. Internally it communicates with the storage 224 and the key-value store 224 (cache) through a socket connection. This can be done, for example, by using a Spring web application having a standard web application Java framework.

The storage 224 in the routing service 108 is used to store all patient information including their contact information. The storage 224 can utilize a relational database (such as PostgreSQL) in order to resolve identifiers provided by the provider application 246 to an entity in the system 100, and consequently look up device fingerprints from the fingerprint service 106.

The key-value store 226 is a temporary storage location (cache) and message broker. The key-value store 226 temporarily holds data that has no permanent place in the regular storage database 224. This is used in ad hoc telemedicine calls where the patient is not an existing entity in storage 224, but a persisted record of the call in progress is still needed so that the routing service 108 is later able to resolve incoming events from the meeting service 110 and message queue 212. The key-value store 226 can be a REDIS cache, for example.

The job processor 228 (or asynchronous task queue) is a long running application that is triggered when messages are added to the shared message queue 212 by the meeting service 110. Every message in the shared message queue 212 is interpreted as a task that can be done by the job processor 228. In this system 100 the job processor 228 parses the events and extracts context about an ongoing video call, such as a telemedicine call. This context is used with the key-value store 226 or database 224 to find the current patient, then fetch the fingerprint from the fingerprint service 106. The job processor 228 then analyzes the fingerprint to determine the best method of reaching the patient. The job processor 228 is the main "router" in the routing service 108. In some implementations, the job processor 228 can be a Java Spring Task Listener or another application framework capable of executing code based on subscription to a message queue.

The job of the notification service 114 is to receive instructions from the routing service 108 via REST HTTP framework and execute them by interfacing with the proper vendors via communications vendor REST server 234. The notification service 114 takes generic JSON messaging instructions and converts them to the requisite format to send push notifications to iOS, Android or desktop devices, or to send an email 236 or SMS 238 communication. Native application push notifications must go through APNs (Apple Push Notification service) and GCM (Google Cloud Messaging). In some instances, the system can use Twilio and Mailchimp to deliver SMS and emails on behalf of the system 100, respectfully.

As discussed previously, the relationship between devices and registered users in the notification service 114 registry is many to one. A user in the registry may be associated with multiple devices, but a known device belongs to one user only at any given time. When the notification service 114 receives a request to associate a device fingerprint with a user, and there is an existing user with a matching device fingerprint, the more recent association takes priority and the former association is revoked. This prevents ambiguity in the ownership of a device and protects privacy by ensuring a user does not receive a call intended for someone else.

Figure 3:
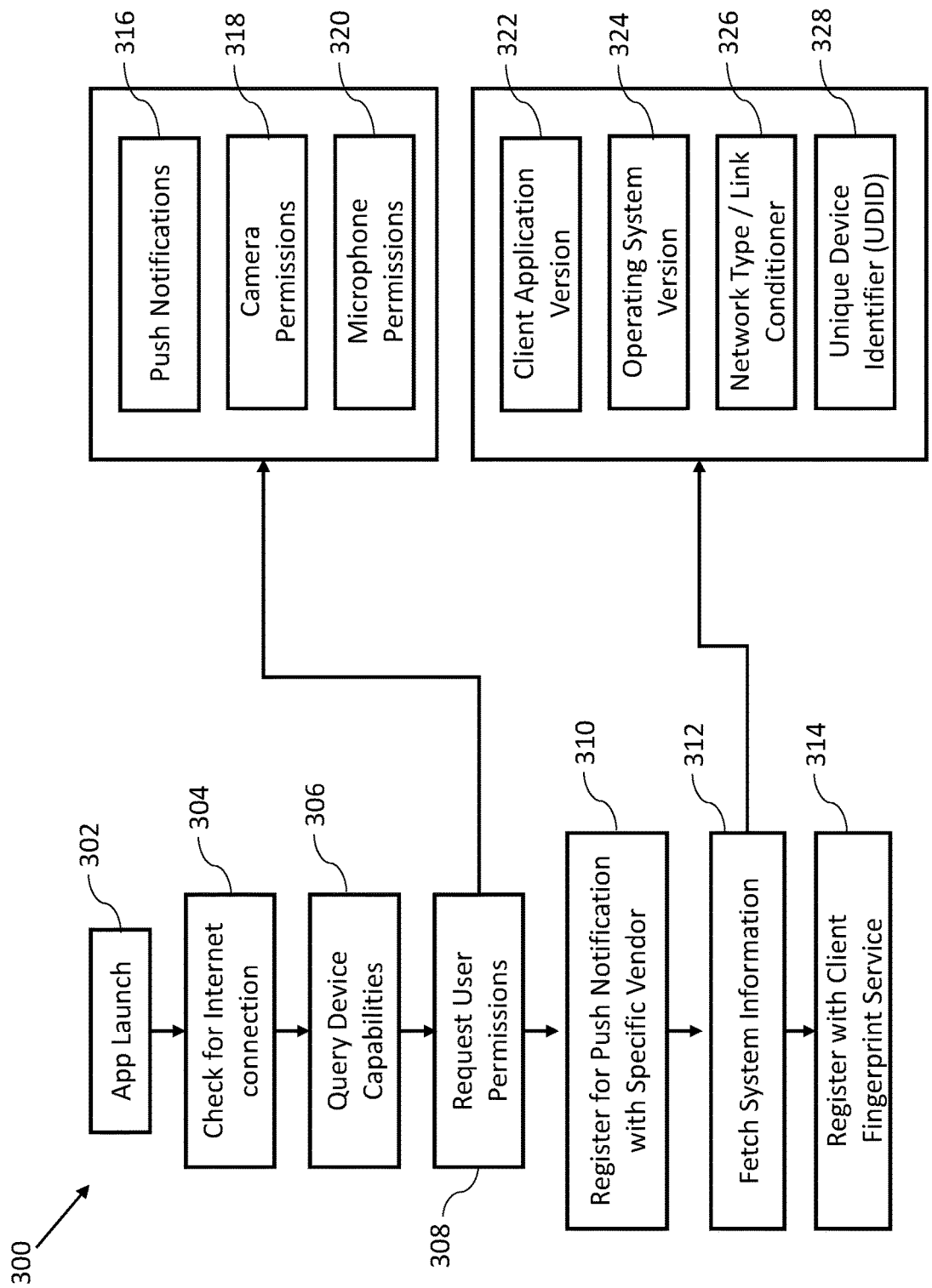
FIG. 3 is an exemplary block diagram showing a process of registering and fingerprinting devices in accordance with the subject technology.

The fingerprint service 106 is responsible for processing a set of input parameters from a device, processing and hashing them, and storing them with associations to the relevant user (as shown in FIG. 3 and discussed in more detail below). The fingerprint service 106 can use a REST HTTP framework to receive registration requests from devices via web application 232, and any kind of database 230 to persist the information. In one example, fingerprint service 106 uses a Dynamo DB for storage and a Python AWS Lambda to receive HTTP requests.

The user and provider applications 220, 246 include three components to support its functions within the system 100, particularly in a telemedicine environment. In particular, it uses a REST HTTP framework 240 to interact with the meeting service 110, a WebRTC interfaces 242 (software component library) to interact with the media room service 112 and other peer-to-peer clients, and an event receiver service 244 to receive remote notifications.

Referring now to FIG. 3, an exemplary block diagram 300 shows the process of registering and fingerprint devices in accordance with the system and processes described herein. The block diagram 300 particularly shows a method where an application is initially launched (step 302) on a user device. After the application is launched, the user device checks for an internet connection at step 304. The system then queries the device capabilities, at step 306.

Next, the application requests user permissions for the system at step 308. The user permissions can include permission for push notifications 316, which allow the system to call the user device to initiate a video call at the appropriate time. The application also requests camera permissions 318 and microphone permissions 320, which allow the application to utilize audio and video capabilities of the device to carry out the video call.

At step 310, the application registers for push notifications with a specific vendor. For example, an Android can register with Firebase Cloud Messaging and an iOS device can register with APNs (each ecosystem having their own push delivery vehicle). The application then fetches system information about the device, at step 312. That can include a current application version 322 of the application being run, and a current operating system version 324 (e.g. an iOS version on the device). The application also gathers information about the network type and/or link conditioner 326, and identifies a unique device identifier (UDID) 328 for that particular device. The user can then be registered, with the fingerprint service 106 using the UDID, at step 314. In this way, device information is stored in a system in a way that allows for the appropriate devices to be identified and reached once a video conference, such as a telemedicine conference, is desired.

As discussed herein, each device's fingerprint is used to determine the platform and therefore the channel by which to reach the patient operating that device. Native mobile applications in the system listen permanently in the background for push events such as incoming video calls. For iOS targets, the push will be sent via voIP (voice over IP) through Apple's APNS which arrives silently, is picked up by the listener, and surfaces as a native incoming call to the device. For Android targets, a push is sent through FCM (Firebase Cloud Messaging) and a banner appears on the user's device. Answering the call, and tapping the banner, respectively, will notify the application to extract the meeting access code in the push payload and use it to join the meeting.

If a call goes out to multiple devices 102, and it is answered on one, the incoming call ("ringing") will be canceled on all other devices 102. As before when the provider joined the call, the event signaling the patient has joined the call is circulated first through the video service (media room service 112), then the routing service 108. The routing service 108 leverages the notification service 114 to determine all devices 102 that were invited to the meeting, and sends another push event out, this time informing the devices 102 that the previous call has been picked up. The event listener inside the native application on each device 102 receives the push, and drops the notification/incoming call from the display. A device 102 that has already answered the call ignores this event. The same process occurs when a provider cancels an outgoing call before the patient has joined anywhere.

If the call is somehow answered simultaneously on multiple devices 102 before the call cancellation can be processed, or an access link is launched while the participant has already joined, the first device 102 to gain access has priority and remains in the meeting. This is possible because although multiple devices 102 are invited, the same secure access code is used for each of them and the video service recognizes these as a single participant who cannot be present twice for the same meeting.

If there are no mobile devices 102 registered for push notifications, the account's registered phone number and email address are used as a fallback to send the single-tap access link which will launch the meeting in the native app if installed. If the native app is not installed, the meeting will be launched in a web browser on the device 102 where the link was tapped. Since the native call experience fails if the user does not provide the requisite audio/video device permissions to the application, these permissions are also stored with the device registry. If permissions have been declined, the recipient is guided to the web browser experience via SMS/email instead of triggering a native call with push.

Therefore disclosed herein is a system and method of facilitating on demand video communication between a number of individuals (e.g. a provider, patient, and individuals related to the patient). The system determines the best way of contacting an individual and providers a notification to one or more of their devices that allows them to connect to the video call in a secure manner. There is no need for a predefined account in an EMR service (e.g. login/username/password). There is no requirement for joining a room once a patient has received the invite link. The video calls are ad-hoc, and can be carried out unscheduled and on-demand. Participants can receive the video call simultaneously on a number of eligible devices, while the system is still single-use access. Users may join the video call at any time after the provider joins, with no extra authentication required and no waiting room necessary. Authentication ensures that no sensitive authentication data or cookies remain once the call is over.

All orientations and arrangements of the components shown herein are used by way of example only. Further, it will be appreciated by those of ordinary skill in the pertinent art that the functions of several elements may, in alternative embodiments, be carried out by fewer elements or a single element. Similarly, in some embodiments, any functional element may perform fewer, or different, operations than those described with respect to the illustrated embodiment. Also, functional elements shown as distinct for purposes of illustration may be incorporated within other functional elements in a particular implementation.

While the subject technology has been described with respect to preferred embodiments, those skilled in the art will readily appreciate that various changes and/or modifications can be made to the subject technology without departing from the spirit or scope of the subject technology. For example, each claim may depend on any or all claims in a multiple dependent manner even though such has not been originally claimed.

What is claimed is:

1. A method of video communication between participants operating one of a plurality of devices, the participants including at least one user and a provider and the devices including at least one user device running a user application and a provider device running a provider application, the method comprising:
   a) generating, by the system, a list of registered users each associated with at least one of the user devices;
   b) generating, by the system, a fingerprint for each of the devices associated with a registered user, each fingerprint being a unique digital identifier for a corresponding device;
   c) requesting, by a provider and from the system, a communication session with at least one user identified by the provider;
   d) in response to the request by the provider, generating, by the system, a participant list of users for the communication session and an access code authorizing access to the communication session, wherein the system sends the access code to the provider;
   e) determining, by the system, all user devices associated with users identified by the provider;
   f) entering, by the provider, the access code in the provider application of the provider device to initiate the communication session;
   g) in response to the provider entering the access code, determining, by the system, a notification type for each device associated with users on the participant list based on the fingerprint for said device, and providing a notification to each device associated with users on the participant list based on the notification type determined for said device, wherein each notification includes a payload containing an access code authorizing access to the communication session; and h) when at least one user device answers the notification and receives the access code, using the access code to join the communication session, by said user device.

2. The method of claim 1, wherein, during step a), devices are registered by the system by one or more of the following ways: providing a URL associated with the system, to the device, the URL then being accessed by the device to register the device; or by running the user application.

3. The method of claim 1 wherein, during step d), the participant list includes users from the list of registered users, and at least one unregistered user.

4. The method of claim 1, wherein, at least one user on the participant list is a patient and the system selects at least one additional user to add to the participant list based on the patient.

5. The method of claim 4, wherein the at least on additional user is a translator, selected by the system based on a native language of the patient.

6. The method of claim 4, wherein the at least one additional user is selected based on a relationship to the patient, including at least one of the following: a relative; a guardian; or a caregiver.

7. The method of claim 1, wherein at least one user on the participant list is a patient and the communication session is a telemedicine session including video communication between participants.

8. The method of claim 1, wherein each fingerprint is an algorithm built from device properties for the corresponding device, account properties for an account of an associated user, and session properties for the communication session.

9. The method of claim 1, wherein, during step g):
when a user is associated with multiple devices, the user receives notifications simultaneously on all associated devices; and
upon answering a notification on one device and joining the communication session by a user, all notifications to other devices associated with said user are terminated.

10. The method of claim 1, wherein, during step h), upon answering a notification on a device the device automatically joins the communication session using the access code.

11. The method of claim 1, wherein, prior to joining the communication session, all participants redeem their access code for an access token based on the access code, the access token authorizing access to a video room for the communication session.

12. The method of claim 11 wherein each participant is associated with a particular access code, and redeeming an access code with a device prevents subsequent redemption of the same access code by a different device.

13. The method of claim 1, wherein the notification types include at least the following: a push notification; an email notification; and a text notification.

\* \* \* \* \*